(12) United States Patent
Froehlich et al.

(10) Patent No.: US 11,931,146 B2
(45) Date of Patent: Mar. 19, 2024

(54) SENSOR CONFIGURATION

(71) Applicant: Luciole Medical AG, Zurich (CH)

(72) Inventors: Juerg Hans Froehlich, Zurich (CH); Fabian Schneider, Zurich (CH); Markus Hugo Muser, Waedenswil (CH); Marco Zahner, Zurich (CH); Dirk Baumann, Zurich (CH)

(73) Assignee: LUCIOLE MEDICAL AG, Zurich (CH)

( * ) Notice: Subject to any disclaimer, the term of this patent is extended or adjusted under 35 U.S.C. 154(b) by 236 days.

(21) Appl. No.: 16/810,387

(22) Filed: Mar. 5, 2020

(65) Prior Publication Data
US 2020/0281510 A1    Sep. 10, 2020

(30) Foreign Application Priority Data
Mar. 5, 2019    (EP) .................................... 19160799

(51) Int. Cl.
*A61B 5/1455*    (2006.01)
*A61B 5/00*    (2006.01)
(Continued)

(52) U.S. Cl.
CPC .......... *A61B 5/1455* (2013.01); *A61B 5/6833* (2013.01); *G01J 3/0218* (2013.01);
(Continued)

(58) Field of Classification Search
CPC .. A61B 5/1455; A61B 5/6833; A61B 5/14551
See application file for complete search history.

(56) References Cited

U.S. PATENT DOCUMENTS

| | | | | |
|---|---|---|---|---|
| 6,014,576 A | * | 1/2000 | Raley | A61B 5/6833 600/344 |
| 10,022,089 B2 | | 7/2018 | Lechot et al. | |
| 2015/0282762 A1 | * | 10/2015 | Lechot | A61B 5/14552 600/344 |

FOREIGN PATENT DOCUMENTS

| | | |
|---|---|---|
| EP | 2916716 A1 | 9/2015 |
| WO | WO 1994/027494 A1 | 12/1994 |
| WO | WO 2012/109661 A1 | 8/2012 |

* cited by examiner

*Primary Examiner* — Marjan Fardanesh
(74) *Attorney, Agent, or Firm* — ALSTON & BIRD LLP

(57) ABSTRACT

The present invention relates to a sensor configuration (1) for non-invasive measurement of parameters of a body tissue with a sensor unit (10) and a sensor mat (12) for detachable placement of the sensor configuration (1) on a body surface (20). Furthermore the sensor unit (10) of the sensor configuration (1) is connectible to a contact head (16), which is designed for electrical contacting of the sensor unit (10) and for supply of light from a light source to the sensor unit (10), the sensor unit (10) being designed as a flexible printed circuit board with optical components, at least comprising a light detector device (2), in order to detect light that is emitted into the body tissue and has passed through the latter, a first contact means (30) and conducting tracks (5) for operative connection of the sensor unit (10) to the contact head (16). The sensor mat (12) of the sensor configuration (1) has a multi-layered structure, with a lower layer (13), which has a lower contact surface for contact on the body surface (20) and an upper contact surface for contact of the sensor unit (10), whereby openings (15, 17) are provided which are aligned with the optical components of the sensor unit (10), and form an optical passage, and with an upper layer (14), which is connected to the upper contact (Continued)

surface of the lower layer (13) in a way detachable from one another.

17 Claims, 4 Drawing Sheets

(51) Int. Cl.
    *G01J 3/02*           (2006.01)
    *G02B 6/42*          (2006.01)
    *A61B 90/30*        (2016.01)

(52) U.S. Cl.
    CPC .......... *G01J 3/0291* (2013.01); *G02B 6/4214* (2013.01); *G02B 6/4281* (2013.01); *A61B 5/14553* (2013.01); *A61B 2090/306* (2016.02); *A61B 2562/0238* (2013.01); *A61B 2562/164* (2013.01); *A61B 2562/166* (2013.01)

SENSOR CONFIGURATION

CROSS REFERENCE TO RELATED APPLICATIONS

This application claims priority to European Patent Application No. 19160799.3, filed on Mar. 5, 2019, the contents of which as are hereby incorporated by reference in its entirety.

BACKGROUND

Related Field

The present invention relates to a sensor configuration, in particular a sensor configuration for non-invasive measurement of body parameters, for example cerebral parameters such as oxygen content of the brain.

Related Art

It is known that, for measurement of body parameters, in particular of cerebral parameters such as concentrations of deoxygenated and oxygenated hemoglobin of the cerebral blood flow or of the tissue oxygenation index, a measuring device is disposed on a body surface, e.g. a head surface, and a measurement is carried out by means of near-infrared spectroscopy (NIRS).

Accordingly, by using light sources which transmit near-infrared light at specific different wavelengths and by measuring changes of the extinction of detected or reflected light, changes in the oxygen concentration of deoxygenated and oxygenated hemoglobin can be monitored. By means of another spectrophotometrical method, the so-called pulse oximetry, the arterial oxygen saturation in the peripheral tissue, for example finger, ear, nose, is able to be determined by monitoring the pulsatile optical extinction changes of the detected light.

Known are NIRS monitoring configurations for non-invasive monitoring, for example of the blood oxygen content, which comprise reusable components and components which are to be disposed of. Thus, for example, known from WO 94/27494 is a spectrophotometrical sensor mat with a flexible layer of foam material for placement on a body surface, which comprises a support frame for receiving sensor elements.

Known from EP 2 916 716 is a non-invasive measuring device for measurement of parameters of a body tissue which provides a sensor unit and a sensor mat for detachable placement on a body part. The sensor unit comprises a sensor arrangement received in a receptacle with a sensor surface oriented on a lower side in direction of the body surface, the sensor unit being closed in a lightproof way by means of a cover or a foil. The receptacle is received in a corresponding cutout made on the bendable and/or compressible sensor mat, whereby the sensor mat rests with a contact surface on the body surface and is connectible thereto by means of an adhesive layer. Sensor unit, sensor mat and cover are connected to one another in a detachable way, whereby sensor mat and cover can be disposable products. Thus the sensor unit comprises a sensor configuration, received in an only partially flexible receptacle, which is designed as a type of flat housing or dish, i.e. comprises a base area and a peripheral walling. The sensor configuration has a contact unit, disposed thereon and firmly connected thereto, for the input and output of electrical and optical signals, the power supply and the connection to an external control and processing unit and/or control unit.

Known from WO 2012/109661 is an NIRS sensor configuration, which has a sensor part with a light source and at least one light detector, as well as a flexible electrical circuit and a connector element. The flexible electrical circuit can be multi-layered and can comprise in a communication layer a plurality of conducting tracks and an EMI shielding for electrical contacting and signal transmission of the sensor configuration with the connector element. The connector element comprises a fiber-optic coupler as optical interface and a line coupler as electrical interface, the two being integrated, for example, in a hybrid connector.

Known from the state of the art are measurement arrangements which, owing to a more or less rigid receptacle for a sensor unit, do not have the desired flexibility to also be able to be placed on extremely curved or bent body surfaces. Furthermore the operative contacting of the included sensor unit is also not solved independently from the measurement configuration.

BRIEF SUMMARY

It is an object of the present invention to provide a non-invasive sensor configuration for determining body parameters, or respectively parameters of body tissue, with which the production costs are reduced, the flexibility of the configuration is increased and the operative contacting is designed independently. Since in the amount of the production costs also the recyclability of at least individual components is to be taken into consideration, aimed for with the invention is to design expensive components in particular to be reusable. In particular homogeneous contact between sensor configuration and surface of the body tissue should be ensured and the sensor configuration should be reusable at least in part.

This object and further objects are achieved by a non-invasive sensor configuration according to the independent claim. Special embodiments and/or variants emerge from the dependent claims.

According to the invention, a sensor configuration for non-invasive measurement of parameters has a sensor unit and a sensor mat for detachable placement, or respectively attachment, of the sensor configuration to one or more curved or bent body surfaces. The sensor unit is thereby connectible to a contact head, which is designed for electrical contacting of the sensor unit and for supply of light from a light source to the sensor unit. Furthermore the sensor unit is designed as a flexible printed circuit board with optical components, which comprise at least one light detector device, in order to detect light which is emitted into the body tissue and has passed through the latter, as well as a first contact means and conducting tracks for operative connection of the sensor unit to the contact head. The sensor mat of the sensor configuration according to the invention has a multi-layered structure, with a lower layer, which has a lower contact surface for support on the body surface and an upper contact surface for support of the sensor unit, whereby openings are provided which are aligned with respect to the optical components of the sensor unit, and form an optical passage. Moreover at least one further layer can be disposed on the lower side of the lower layer, and thereby turned toward the body surface, which further layer has optically transparent sections in the regions of the openings and hence forms a kind of foil window with respect to the light input or respectively light output sections. Optically transparent means that a quantity of light can pass through such a layer, which quantity is sufficient, for example, for an NIRS analysis. Other regions of the layer can, on the other hand, be optically not transparent. Alternatively, a first optically transparent layer and a further optically not transparent layer with corresponding optical passages can be disposed on the lower side of the lower layer of the sensor mat. The optically not transparent sections, or respectively the optically not transparent further layer, provide a kind of insulating layer, which are disposed between the optically active regions of the sensor configuration and thus prevent an influencing of the light detection through, for example, lateral light incidence and/or background light. Such a covering of the optically active components has an advantageous effect with regard to a sterile sensor configuration. The sensor mat further comprises an upper layer, which is connected to the upper contact surface of the lower layer in a way detachable from one another. An outer shape of the sensor configuration is designed with notches or respectively indentations so that this shape is able to be arranged on the most diverse body surfaces and provides in particular good wearing comfort.

The sensor configuration can consist of components able to be separated from one another, whereby the contact head and the sensor unit enter into an operative connection, and the sensor mat is designed in order to attach the sensor unit connected thereto easily and securely to the skin of a person to be examined. It is more economical to design the sensor unit and/or the contact head as reusable elements, while at the same time fulfilling the high requirements as to hygiene and sterilization for use in health care. The sensor unit is thus able to be accommodated in the multi-layered sensor mat, whose individual layers are separable from one another, so that the sensor unit received in between can be removed and, after preparatory steps, can be used again.

The sensor unit of an optoelectronic sensor configuration of this kind is, according to the invention, designed as flexible or flex-rigid printed circuit board, also designated as flexprint. Disposed on the sensor unit can be outlets of one or more light sources, such as, for instance, light-emitting diodes, laser diodes, or a plurality of light sources themselves, and, spaced apart therefrom, one or more sensor surfaces, e.g. light detectors designed as photodiodes, as well as electrical lines, which conduct e.g. light from the light source or the light sources or electrical signals to and from the elements of the sensor unit. Further elements can likewise be provided, for example a control unit, which measures, via correspondingly provided sensor surfaces, a background light respectively between individual light pulses of the light source and/or the electrical current. Thus the control unit, via the sensor surfaces, can automatically measure a background light in each case between laser light pulses, based on the light source, which is used as adjustment for the measured light during the laser light pulses. With a partially or completely detached sensor configuration, the background light changes, so that either an interference signal or an interference automatic mechanism can be generated or triggered, which can lead to the automatic switching off of the light-emitting, or respectively laser, diodes. Furthermore the control unit can be used for further calibration or measurement tasks.

In a supplementary way, moreover, a means for capturing temperature and/or thermal flux can be provided. For example, determining the temperature of the tissue to be examined by means of NIRS can be foreseen, which is based on a temperature dependence of the water absorption spectrum. Furthermore one of the included sensor surfaces can also be used, however, to capture the temperature of a light source integrated in the sensor configuration for verification of the temperature influence on the emission characteristics of the light source, e.g. of the LEDs, and of the determined measurement results. It is known that heat from a light source positioned close to the body surface is found to be unpleasant by a patient, or respectively, with too high a temperature, even a failure of individual components of the sensor configuration can occur.

Preferably provided as light source are at least four different light-emitting, or respectively laser, diodes of different wavelengths, which can be switched on and off in a phased way. The light source is operable in a selective way, in order to conduct or to emit in particular infrared light, whereby the light source either generates light signals itself as a light source integrated in the sensor configuration, or generates light signals at a position outside the sensor configuration, and which are conducted to the sensor configuration by means of a fiber-optical element. Thus one or more light sources, designed as light-emitting diodes or laser diodes, can be directly integrated in the contact head, so that losses of the light-emitting diodes at optical coupling points can be avoided. These integrated light sources will be designated as internal light sources.

Transmission losses are prevented to a large extent when the light from a remote light source is emitted by means of fiber optics via the contact head into the body tissue to be examined. In an advantageous way, in particular with a light source positioned outside the sensor configuration, i.e. an external light source, the examination room or respectively the blood flow is prevented from being influenced by heat build-up from the light source.

The light detectors, in particular the one or more photodiodes, are disposed on the sensor unit, so that these light detectors are separated from the light input point by some mm to more than 20 mm. Preferably a spacing apart of the light input point from at least a first photodiode, referred to as near detectors, amounts to about 20 mm, and to one or more further second photodiodes about 40 mm, which can be designated as far detectors. The relative position and the spacing apart of the light detectors from the light input point or points can be based on the size of the object to be examined. The number of photodiodes in the light detectors can vary depending upon application. A plurality of photodiodes can be used to monitor different depths of the blood oxygenation in the subject, or can be used as reference detectors, for example to compensate, in an algorithm, interference effects of the detected signals.

With regard to the sensor unit, designated generally as flexprint is a flexible or flex-rigid printed circuit board having printed conducting tracks, with a substrate made of an insulating polymer material, with fibers, disposed thereon or respectively embedded therein, of an electrically conductive material to form a flexible circuit. A flexible circuit in combination with a flexible substrate improves the flexibility of such a sensor unit. The sensor unit designed as flexible printed circuit board can be constructed in a multi-layered way, in particular with a communication layer, for example comprising a flexible copper-clad laminate, as well as with cover layers or respectively insulating layers and corresponding adhesive layers. The multiplicity of layers of the sensor unit can be laminated, joined or connected together in another way in order to form a single structure. The number of layers can also vary. For example, one or more layers can have optically transparent sections at least in alignment with respect to the regions of the light input points and the light detector surfaces, through which a quantity of light can pass. For example, the optically transparent section can contain an electrically conducting wire mesh, e.g. a copper wire mesh. Other sections of the sensor unit are optically not transparent, and can be made, for example, of a copper metal foil. A sensor unit designed in this way is characterized by a minimal weight and volume, allows a great freedom of design, and provides dynamic and mechanical strength.

In one embodiment, reinforcement elements are provided on the sensor unit, at least section-wise. These reinforcement elements, also referred to as stiffeners, can be designed as shaped pieces made of a rigid material, in particular in the form of polymer thickenings or swellings, which stiffen the flexible printed circuit board in desired regions, for example in the region of the photodiodes. For further stabilization of the form and of the evenness of the sensor unit, a copper net can be provided as woven layer. The provided copper net can also provide a type of shielding against electromagnetic interference.

The sensor unit is preferably designed as a body stretched along a longitudinal axis. The design of the sensor unit takes into consideration rounded transitions and correspondingly shaped sections, so that breaking points are avoided when the sensor unit is disposed in an extreme curvature or in a severely bent way, for example is placed around a finger.

The sensor unit designed as elongated body has preferably tabs, which extend substantially perpendicular to both sides and/or along the longitudinal axis of the body. The tabs, also referred to as noses, as well as the basic design of the body of the sensor unit make possible its even contact surface on the sensor mat. The optical components, i.e. light detector devices and/or emitters, hereby lie, for example on optically transparent surfaces or respectively windows of the sensor mat, or directly on the body surface, for an efficient measurement. With the design of the sensor unit according to the invention, it is not necessary for the sensor unit to be received in a more or less rigid receptacle and fixed therein by means of silicon casting in order to be then received on or in a sensor mat. The flexibility increases accordingly.

According to one embodiment, the sensor unit comprises the first contact means with a contact geometry that is designed for electrical contacting and for connecting to the contact head. Hence the first contact means provides an operative connection to the electrical supply of the sensor unit and to the connection with a light source, as well as for transmission of detected signals. In other words, the first contact means is a coupling element or respectively a connector element, which can be detachably connected to a correspondingly designed mating piece. The connection can be designed inter alia as plug contact or catch. In a preferred embodiment, the contact geometry comprises for this purpose magnetic and electrical contact elements. Thus the first contact means can be designed as a contact ring, which is designed on the sensor unit, designed as flexible or flex-rigid printed circuit board, in a position that is suitable to be brought into contact with the contact head (still to be explained more closely). In particular the contact ring can have the form of a PCB ring, comprising a multiplicity of elements for electrical and mechanical, or respectively magnetic, contacting with counter-pieces provided on the contact head. It is thereby foreseen that the connectible contact head is positionable in a predetermined orientation relative to the sensor unit. In particular an alignment aid, for example in the form of a positioning ring, can be disposed on the contact ring, which predefines a predetermined alignment of the connectible contact head through an asymmetrical shape or respectively shaped sections. In this way cables, which are connected to the contact head for electrical and/or optical connection, can be aligned in an orientation such that a person is not disturbed by the attached sensor configuration. In particular, the positioning ring can be adhered to the sensor unit.

The first contact means has the contact geometry, comprising electrical and magnetic contact elements. In particular the contact elements can be integrated on a contact ring, whereby the contact geometry is provided in an arrangement on an annular surface, so that, available are, for example, a plurality of electrical contact elements, in particular contact points, for electrical contacting of the sensor surfaces, i.e. of the photodiodes of the near and/or far detectors, and one or more magnetically effective contact elements. The magnetically effective contact elements can be designed as tin points. Preferably, electrical and magnetic contact elements are positioned in an alternating sequence, which means that an electrical contact element is situated between adjacent magnetic contact elements. A mutual influencing of electrical contact elements is thereby prevented. The magnetic contact elements are selected in such a way that a secure contacting between sensor unit and contact head exists. It can be foreseen furthermore that the secure contacting of sensor unit and contact head is detected and indicated by means of corresponding detection means or respectively control means.

The sensor unit of the sensor configuration according to the invention can be produced in a simple way in that prefabricated components merely have to be brought into connection to one another, preferably by "pick and place" steps.

The sensor unit and the contact head, operatively connectible thereto, can be attached in a detachable way to the sensor mat. The sensor mat has recesses, or respectively openings, or transparent windows, which are disposed and designed in a way corresponding to the optical components of the sensor unit, i.e. light detector device and/or emitter. Basically the sensor mat is designed as an elongated flat mat, preferably with a multi-layered structure, whereby at least one foam layer is included, made out of a thin, biocompatible foam material, with an adhesive layer disposed on one side or both sides.

A lower layer is thereby included, which has openings or respectively passages or also transparent windows in the region of the sensor surfaces, i.e. the photodiodes, and the coupling region or respectively the light-emitting surface of the light, i.e. the emitter, and which, with an underside, is in contact with the body surface and is attachable thereon by means of an adhesive layer. The corresponding upper side is likewise adhering, so that the sensor unit resting thereon is held by means of the tabs or respectively noses designed thereon. In addition, at least one further layer is included, i.e. an upper layer, which has only one opening in the region of the light input, i.e. in the region of the contact head. The upper layer comprises a lower adhesive layer, which is in adhesive connection to the upper side of the lower layer, so that the sensor unit is received in a way securely positioned there-between. The multi-layered sensor mat can be designed as single-use unit, i.e. after a measurement the sensor configuration can be removed from the body surface and the individual components, i.e. sensor unit, sensor mat and contact head, can be separated from one another, and the sensor mat can be disposed of or respectively recycled.

Preferably the sensor mat is designed flexible or respectively bendable, so that the sensor mat is adaptable to the body surface and adapts itself to curves, protrusions or depressions thereof. The design of the sensor mat provides for an outer circumference which has, for example, notches and/or thin areas, which are provided along the entire outer circumference. In particular the outer circumference can be designed in the form of wings in those regions at which the tabs, or respectively noses, of the sensor unit come to lie on the sensor mat, so that a simple adaptation of the sensor mat to the contour of the body surface is made possible.

In an alternative embodiment of the sensor mat, a middle layer can be provided between the lower layer and the upper layer.

In one embodiment, for measurement of body parameters, the sensor configuration is thereby activated in that a coupling of light waves and an electrical contacting take place by means of the contact head connected to the sensor unit. The contact head connectible to the sensor unit comprises a housing, at least two contact means, which have a contact geometry corresponding to the first contact means of the sensor unit, electrical lines, which are fixable in the housing and which are connectible in a conductive way to electrical contact elements of the second contact means. The contact head comprises means of supplying and guiding light in one direction, which is directed perpendicular to the body surface, and a light emitting surface via which the light is emitted into the body tissue. In one embodiment, the means comprise a fiber-optical element, in order to conduct light from an external light source, and a deflector element, in order to deflect the light led in one direction into the direction perpendicular to the body surface. The deflector element can be provided as reflection surface, in order to deflect the light led in from a first direction into a second direction, which is directed substantially perpendicular to the body surface, and which light is emitted into the body tissue via a light-emitting surface.

Foreseen in an alternative embodiment is that the means for providing and guiding light comprise an internal light source, for example in the form of one or more light-emitting, or respectively laser, diodes, which is/are integrated as internal light source in the contact head itself, and a light-guiding element, so that light emitted therefrom is directed in a direction perpendicular to the body surface and is emitted via a light-emitting surface. Thus in such an embodiment no fiber optics are required, but instead the light waves going out from the internal light source are emitted by means of the light-guide element via the light-emitting surface into the body tissue in contact therewith.

Furthermore it can be foreseen that an energy source received in the contact head is provided for electrical contacting of the internal light source integrated in the contact head and/or of the sensor unit connectible to the contact head, so that the electrical lines run inside the contact head for electrical contacting of the at least one light detector device of the sensor configuration, while no external connections are required. A transmission of the signals, i.e. data transmission, from the at least one light detector device and/or control unit to an external control and/or processing unit can take place by means of wireless communication.

Provided control means ensure that no light is emitted when no contact to a body surface exists, or respectively when the contact head is not securely connected to the sensor unit. For this purpose control means are provided in order to measure a background light, the measurement of the background light being used to achieve an emergency switching off of the sensor configuration. As soon as the value, or respectively intensity, of the background light has exceeded a predetermined maximal value, the one or more light sources are switched off, in order to be sure that no risk exists when the sensor configuration has detached intentionally or unintentionally, partially or completely, from the body surface.

The electrical lines and the light supplies, e.g. designed in fiber optics with at least one optical fiber, can be integrated in a hybrid cable, which is fixable to the contact head.

Provided for electrical contacting of the sensor unit of the sensor configuration according to the invention are the second contact means, which are able to be accommodated as separate annular components in the housing of the contact head. The second contact means comprise, in one embodiment, a first contact ring, on which are disposed, on a first side, spring contact pins in a predetermined arrangement and, on a second side, connector elements, which form a plug contact with a mating part provided on the electrical lines, and a second contact ring, which has through-holes, through which the spring contact pins extend, and on which, on a first side, magnetic contact elements are disposed, which are able to be brought into contact with those of the first contact means.

Accordingly, the second contact means are designed with a contact geometry complementary to the first contact means. The second contact means can be designed ring-shaped, in particular as substantially annular printed circuit board, i.e. as PCB, whereby connecting elements, preferably spring contact pins, are provided on a first side for electrical contacting. The connecting elements are positioned in such a way on the second contact means, in a configuration on one side, that they are able to be brought into contact at a predetermined orientation with the electrical contact elements of the first contact means, whereby the exact orientation can be provided through the shaping of the second contact means. The second contact means can be placed on an underside of the contact head, or respectively of the housing, i.e. approximately parallel to the body surface. Connector elements are disposed on the second contact means, in particular a micro plug, on the second side, and thereby opposite the first side having the spring contact pins. Thus the electrical lines can be brought into conductive contact with the spring contact pins via a plug connection.

Furthermore the second contact means comprise the second contact ring, which has on an annular surface a corresponding arrangement of magnet elements and through holes, which are designed in such a way that through these the connecting elements, i.e. the spring contact pins, can be inserted so that they project above the annular surface. In particular through holes and magnet elements alternate on the annular surface of the second ring, so that a secure electrical and magnetic contacting of the contact head with the counterpieces on the first contact means of the sensor unit is provided.

In an embodiment with an external light source, a fiber-optical element is fixable on the contact head, which element comprises at least one optical fiber, which is fixed in the housing or in an element able to be accommodated in the housing. Accordingly the contact head provides, in additional to the electrical contacting, also a guiding of light, for example from a remote light source, and a coupling of the light waves in the tissue to be examined. Light, e.g. near infrared light, is directed along the fiber-optical element, along a first direction and is deflected on a reflection surface, so that the light exits out of the contact head, on the light emission face, in a second direction, generally perpendicular to the first direction and in particular perpendicular to the body surface. Thus light is projected out of the contact head onto an object, for example via a correspondingly designed coupling element, which can be brought into direct contact with the body surface. The fiber-optical element comprises one or more optical fibers, which is/are received in a bore in the housing of the contact head, or in a retaining element able to be accommodated therein, and are held therein. The retaining element can be in direct contact with a deflector element, which provides the reflection surface, so that light beams are correspondingly deflected and emitted into the tissue to be examined substantially perpendicularly via a wide area contact. For example, the deflector element can be designed as a prism.

The deflector element can be designed as a cylinder with a closed beveled end face. For this purpose the deflector element is designed as a galvanized plastic part, whereby the light waves emitted out of the fiber-optical element are deflected and/or reflected on the provided reflection surface in the direction of the light emission surface.

Alternatively the deflector element is designed as a hollow cylinder with a closed semispherical end face. The deflector element is made in particular of a reflecting material. The bore for receiving the fiber-optical element thereby comes out at the semispherical end face, whereby emitted light is deflected at the semispherical reflection surface in the direction of the second direction and thereby in the direction of the light emitting surface.

According to the invention, the contact head complementary to the sensor unit is designed as a separate unit, so that an optimal production is possible, in a way independent from the further components of the sensor configuration. Only the contact means of contact head and sensor unit are harmonized with one another. Accordingly a contacting of the sensor unit of the sensor configuration according to the invention is also possible in a simple way, likewise taking into account local conditions, in order to design the orientation of the incoming and outgoing lines in as comfortable a way as possible for a patient.

BRIEF DESCRIPTION OF THE DRAWINGS

Preferred embodiments of the invention are presented in the following with reference to the drawings, which only serve explanatory purposes and are not to be interpreted as limiting. Features of the invention apparent from the drawings should be considered individually and in any combination as belonging to the disclosure of the invention.

BRIEF DESCRIPTION OF VARIOUS EMBODIMENTS

In the following description of a sensor configuration according to the present invention, a lower side is to be understood as a side turned toward a body surface, and an upper side is to be understood as a side opposite the lower side. Upper and lower sides are thereby at least approximately parallel to a body surface or respectively at least section-wise parallel.

Figure 1:
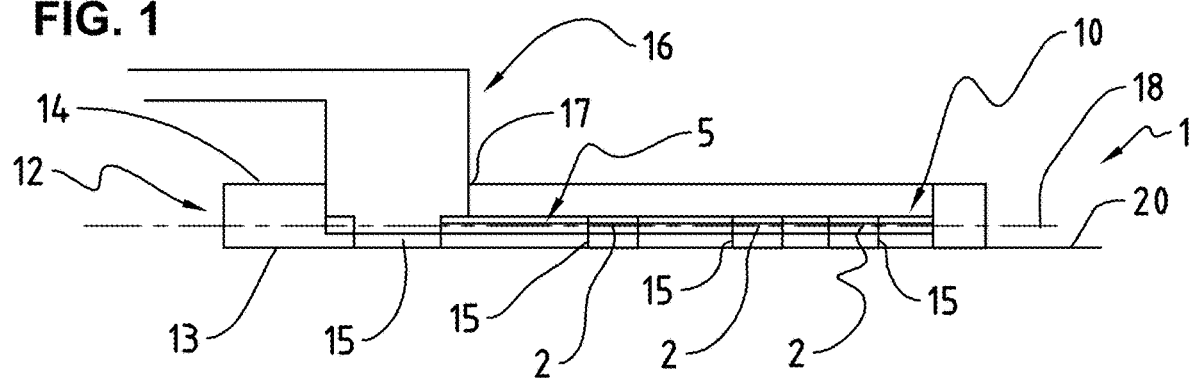
FIG. 1 shows a schematic representation in the form of a sectional view through a sensor configuration according to the present invention.

Shown schematically in FIG. 1 is the structure of a sensor configuration 1 according to the invention for non-invasive measurement of parameters of a body tissue with a sensor unit 10 and a sensor mat 12 for detachable placement of the sensor configuration 1 on a body surface 20.

In the embodiment shown, the sensor configuration 1 comprises essentially the reusable sensor unit 10, the sensor mat 12 and a contact head 16 for electrical and optical contacting of the sensor configuration 1. The sensor unit 10 has light detector devices 2 (also designated as measurement surfaces), spaced apart from the position of the contact head 16, and conducting tracks 5. Further elements, for example control units, can be provided in the sensor configuration 1. From a light source via the contact head 16, or via a light source disposed directly on the sensor unit 10 or respectively in the contact head 16, with a plurality of light-emitting or respectively laser diodes, preferably four laser diodes, light can be emitted in each case with different wavelengths in near infrared range (NIRS) for measurement of parameters, preferably in a time-phased way. Used as sensor surfaces 2 are e.g. photodiodes. The sensor unit 10 is designed as an elongated flat body shape along a longitudinal axis 18, with a defined outer contour, which is harmonized or coordinated with the outer contour of the included elements and with the body surface to be applied. The sensor unit 10 is designed as flexible printed circuit board and thus bendable to a certain degree. The sensor unit 10 is received on the sensor mat 12, which comprises a lower layer 13 and an upper layer 14.

The lower layer 13 has on a lower side a base area with a plurality of openings 15, which provide a passage for light. The base area is turned toward the body surface 20. The lower side of the base area is designed as contact surface for support on the body surface 20. The base area encompasses the sensor unit 10 completely and in its outer contour is harmonized with or coordinated with the sensor unit 10, whereby in particular wings are provided, which are provided substantially in a way perpendicular to both sides of the longitudinal axis 18. The shape of the sensor mat 12 determines the size of the contact surface and thus the support on the body surface 20 for fixing of the sensor configuration 1. Disposed on the contact surface of the lower layer 13 is an adhesive layer.

The upper side of the lower layer 13 is in contact with the upper layer 14 of the multi-layered sensor mat 12; in particular lower layer 13 and upper layer 14 are detachably connected to one another on the contact surface, for example through an adhesive layer. The upper layer 14 also has an opening 17, through which the contact head 16 is led at least partially. Thus the upper layer 14 of the sensor mat 12 covers the sensor unit 10 as a cover. The sensor mat 12 is designed flexible, in order to be able to adapt to the contour of the body surface 20.

The sensor mat 12 is provided as a single-use unit and is disposed of after being used one time. The multi-layered sensor mat 12 has at least one foam layer.

Figure 2A:
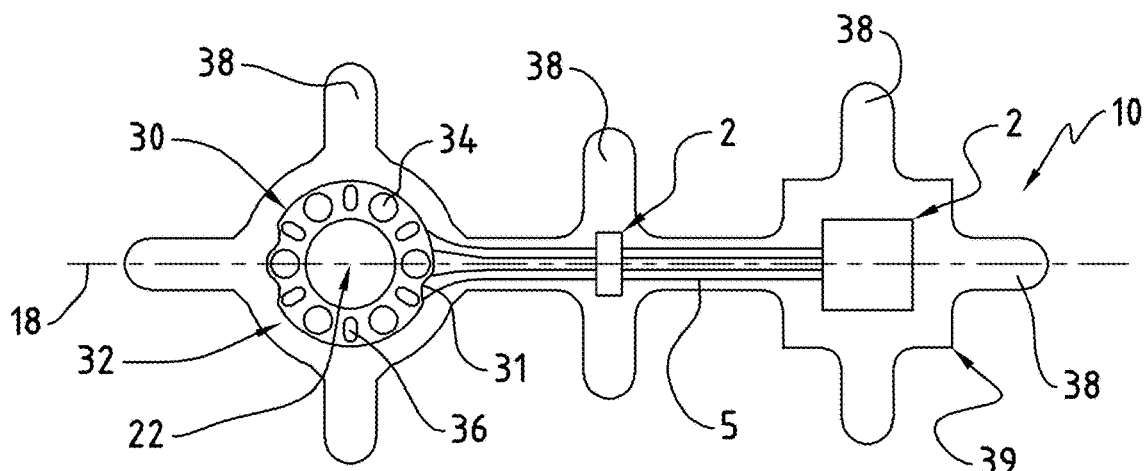
FIG. 2a shows a sensor unit of a sensor configuration according to the invention, designed as flexible printed circuit board with the first contact means for electrical and optical contacting.
Figure 2B:
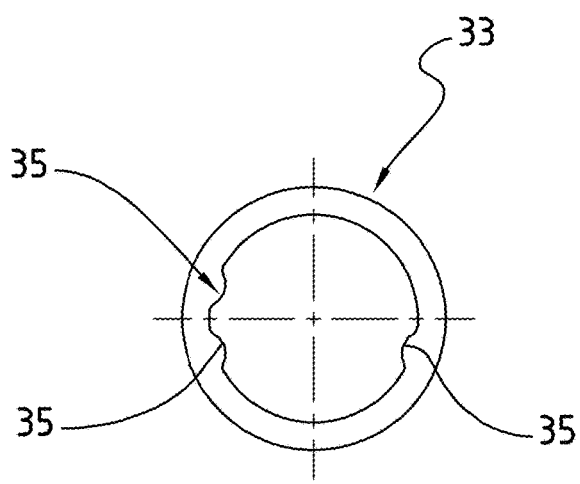
FIG. 2b shows a positioning ring, able to be disposed on the sensor unit according to FIG. 2a, FIG. 3 shows a bottom view of a sensor mat of a sensor configuration according to the invention.

Shown in FIG. 2a is a schematic view of the sensor unit 10, which is designed as flexible or flex-rigid printed circuit board. The sensor unit 10 is designed in the form of a flat body stretched along the longitudinal axis 18, whereby first and second light detector devices 2, or respectively sensor surfaces 2, are arranged. The light detector devices 2 are positioned at different separating distances from a light coupling point on a contact surface 22, or respectively light emitting surface or light coupling point. The separating distance is based on the circumstances of the application, and in the embodiment shown refers to light detector devices 2 for measuring near and deeper body tissues in body surfaces 20. Conducting tracks 5 extend along the longitudinal axis 18, which are set up both for signal transmission and for electrical contacting, whereby a first contact means 30 with a contact geometry 32 is provided. The first contact means 30 is designed substantially annular, in a way integral with the sensor unit 10 designed as flexible or flex-rigid printed circuit board. Provided in one or more regions on an outer circumference of the largely annular first contact means 30 are positioning elements 31, for example in the form of indentations on the circumference. The shape of the annular first contact means 30 is designed to complement the shape of a positioning ring 33, which is shown in FIG. 2b. The positioning ring 33 has on an inner circumference the correspondingly designed positioning elements 35, for example protrusions, which allow the positioning ring 33 to be positioned and fixed in a predetermined orientation on the sensor unit 10. The positioning ring 33 allows the contact head 16, to be contacted with the sensor unit 10, to be positionable in a predetermined orientation by means of the shaping of the positioning ring 33. Disposed on an annular surface of the first contact means 30 are magnetic contact elements 34 and electrical contact elements 36 in an arrangement according to the contact geometry 32. The electrical contact elements 36 can be contacted in an electrically conductive way for activation of the light detector devices 2 via the conducting tracks 5. The magnetic contact elements 34 form, together with a corresponding counter-piece, provided on the contact head 16, a detachable connection of the sensor unit 10 to the contact head 16, as will be described later. The electrical contacting of the sensor unit 10 is provided by means of the magnetic coupling.

Tabs 38, or respectively noses, are formed on the elongated body of the sensor unit 10, in particular in the region of the optical components or respectively the sensor surfaces 2, as well as at the light coupling point 22, which tabs extend perpendicularly and/or along the longitudinal axis 18. The shaped-on tabs 38 form a contact surface on the multi-layered sensor mat 12. Not discernible in the perspective shown, the sensor unit 10, designed as flexible or flex-rigid printed circuit board, has reinforcement elements 39, which can be designed as material thickenings or swellings at positions of the optical components.

Figure 3:
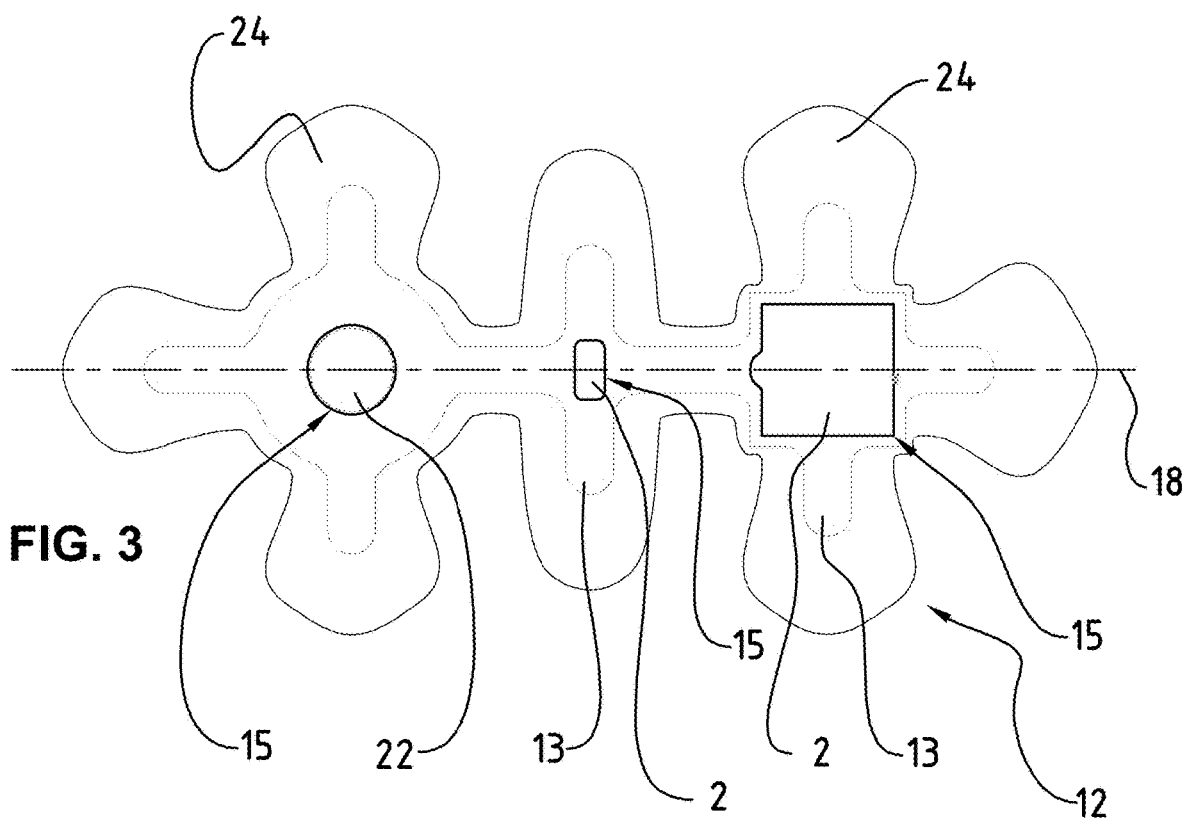

Shown in FIG. 3 is a view of the sensor mat 12 seen from below, so that the base area of the lower layer 13 is visible. The sensor mat 12 is designed as elongated flat body, which extends in particular along the longitudinal axis 18. The base area, which forms the contact surface for support on the body surface 20, has a plurality of openings 15 in the regions at which optical components of the sensor unit 10 are provided, for example the light coupling point 22 and the light detector devices 2. The outer contour of the sensor mat 12 can have different shapes; in particular wings can be provided in regions of the optical components, which wings are designated in general by 24 and which extend at least in part perpendicular to the longitudinal axis 18.

Figure 4:
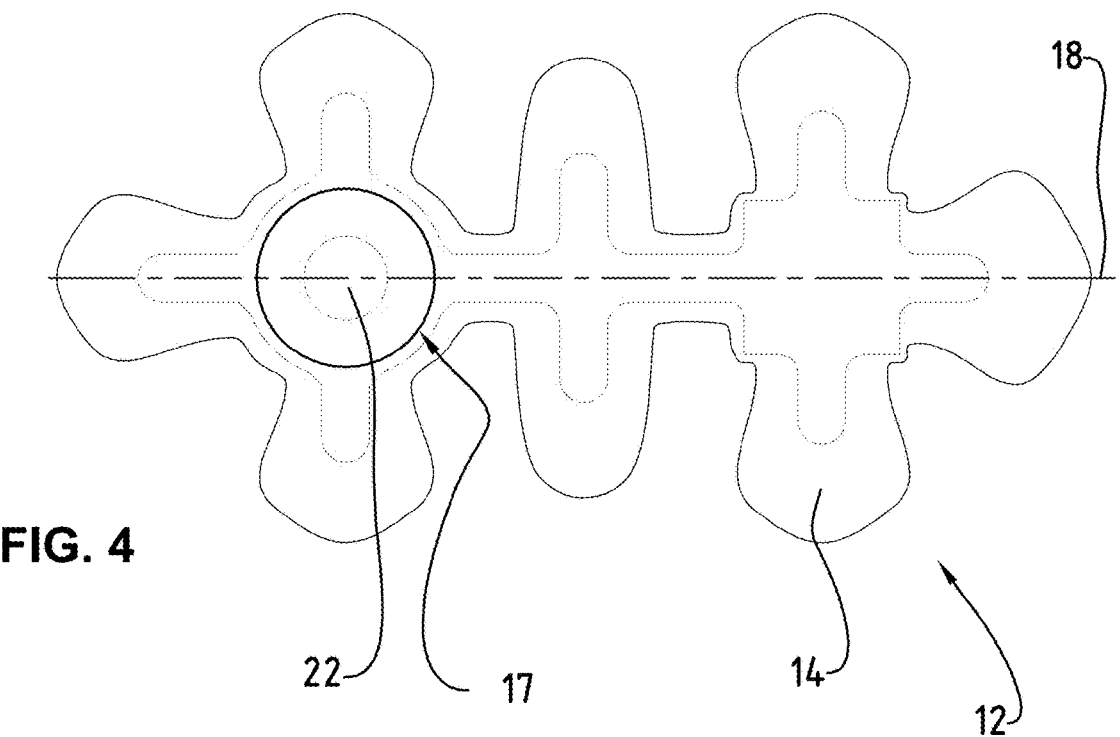
FIG. 4 shows a top view of a sensor mat of a sensor configuration according to the invention.

Shown in FIG. 4 is a view of the upper layer 14 of the sensor mat 12, which corresponds substantially to that of the lower layer 13 with respect to the shape of the outer contour. However there is just one opening 17 in the upper layer 14, made in the region of the contact surface 22 or respectively the light coupling point 22, which opening provides a passage for light to be irradiated into the body surface 20 located beneath.

Figure 5:
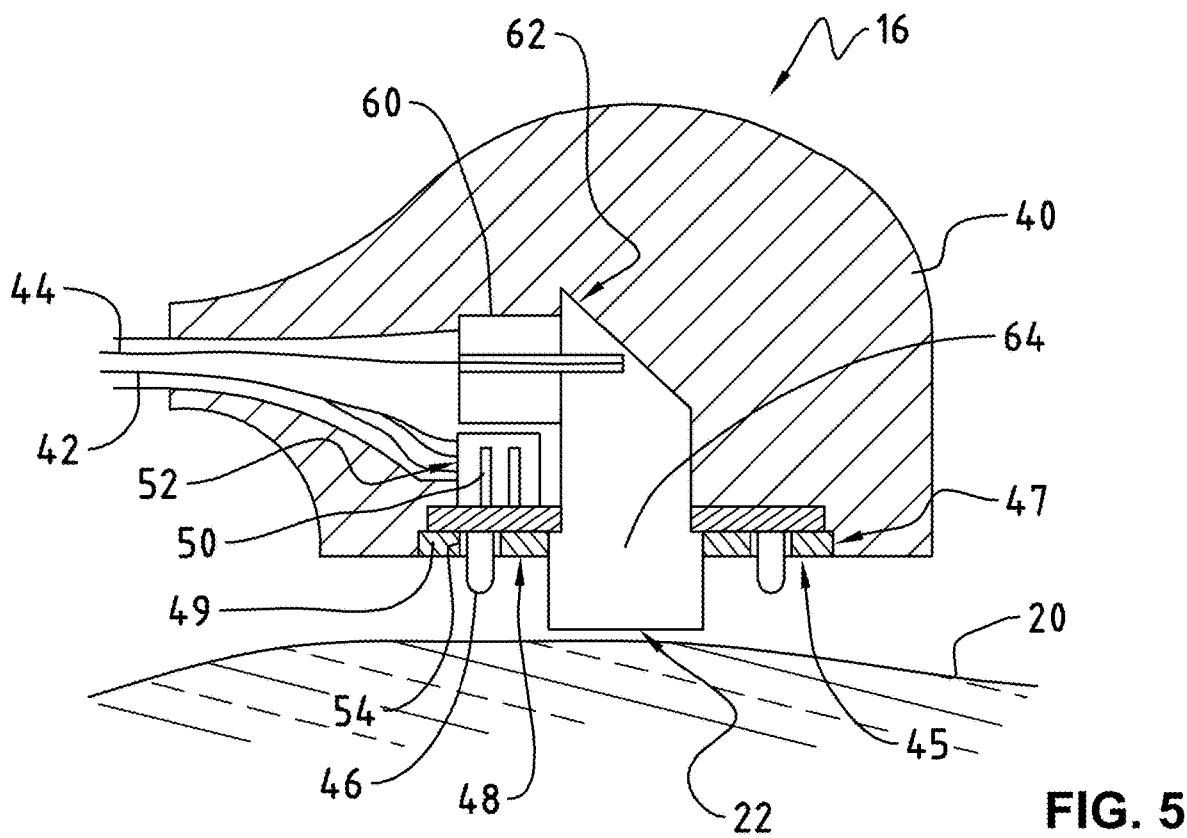
FIG. 5 shows a detail view in the form of a sectional view of a contact head according to one embodiment.

Shown in FIG. 5 is a detailed view as sectional view of a contact head 16 according to a first embodiment, which can be brought into operative connection to the sensor unit 10. The contact head 16 comprises a housing 40, in which, in a receptacle or receiving area (not shown in more detail), electrical lines 42 and a fiber-optical element 44 are able to be accommodated and fixable. The electrical lines 42 are in electrically conductive connection to spring contact pins 46, which are provided on the second contact means 47. In the embodiment shown, the spring contact pins 46 protrude downward out of a first contact ring 48 of the second contact means 47 and are connected on an opposite side of the first contact ring 48, in an electrically conductive way, by means of connector elements 50, to the electrical lines 42, for example by means of a plug 52 disposed thereon. Disposed on the first contact ring 48 can be a second contact ring 49, which has through holes 54, through which the spring contact pins 46 extend. Furthermore disposed on a lower side of the second contact ring 49 are magnet elements or respectively magnetic contact elements 45, which are positioned in an arrangement complementary to the contact geometry 32 of the first contact means 30 (not shown).

Shown furthermore in FIG. 5 is that the fiber-optical element 44 is received and fixed in a retaining element 60, able to be received in the housing 40, whereby light emitted out of the fiber-optical element 44 in one direction is deflected, or respectively reflected, in a second direction on a provided reflection surface 62, which second direction is oriented substantially perpendicular to the first direction, and exits substantially perpendicular to the body surface 20 through the contact surface 22 or respectively light coupling point 22. The reflection surface 62 is formed by an oblique closed end of a deflector element 64, designed as cylinder, which is received and held in the housing 40 of the contact head 16.

Figure 6:
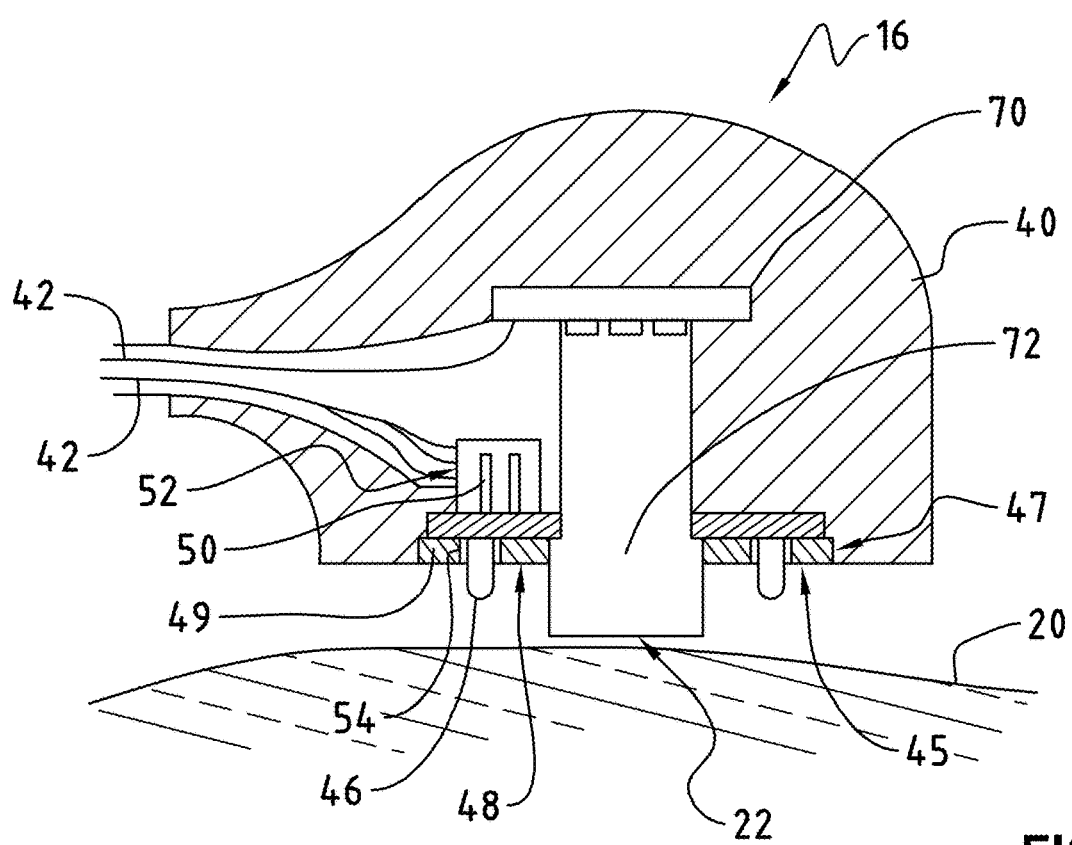
FIG. 6 shows a detail view in the form of a sectional view of a contact head in a second embodiment.

Shown in FIG. 6 is an alternative embodiment of the contact head 16, whereby in particular an internal light source 70 is provided in the form of light-emitting diodes or respectively laser diodes in the housing 40. The contact of the contact head 16 to the contact geometry 32 of the first contact means 30 of the sensor unit 10 corresponds to that of the embodiment shown in FIG. 5. Shown schematically in FIG. 6 is the internal light source 70, which can be electrically contacted by means of electrical lines 42. The light coming out of the internal light source 70, preferably light waves with different wavelengths, is guided along a light guide element 72 in body surface 20 direction. The light guide element 72 can be designed as a cylinder made of a light-conducting material, for example of polycarbonate, and is able to be accommodated in the contact head 16.

Figure 7:
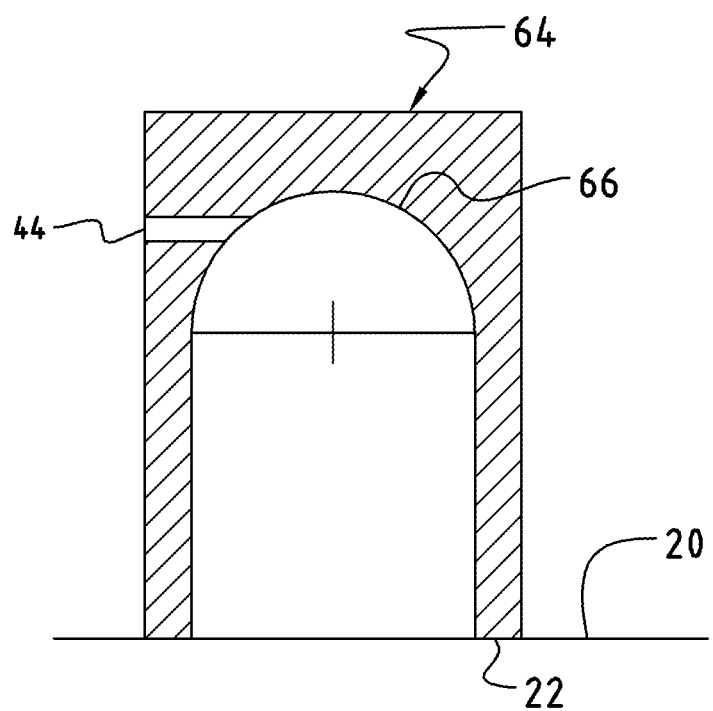
FIG. 7 shows a detail view of a deflector element of the contact head according to one embodiment.

Shown in FIG. 7 is an embodiment of a deflector element 64. The deflector element 64 is designed as a separate element, which is able to be accommodated in the contact head 16 and fixable therein. In the embodiment shown, the deflector element 62 is designed as hollow cylinder with a semispherical closed end 66. A contact for the fiber-optical element 44 comes out into this semispherical end 66, so that light coming out of the fiber-optical element 44 is reflected on the semispherical form and is deflected substantially perpendicular to the fiber-optical element 44, in order to be emitted from the light coupling point 22 or respectively the contact surface 22 into the body surface 20 in contact therewith.

The invention claimed is:

1. Sensor configuration (1) for non-invasive measurement of parameters of a body tissue, the sensor configuration comprising:

a sensor unit (10), a sensor mat (12) for detachable placement of the sensor configuration (1) on a body surface (20) having the body tissue, and a contact head (16) detachably attached to the sensor unit (10), wherein:

the sensor unit (10) comprises:
(a) a flexible printed circuit board having conducting tracks (5) and a longitudinal axis (18),
(b) at least one light detector device (2) for detecting light that has been emitted into the body tissue and has passed through the latter, and
(c) an annular shaped first contact (30) having electrical contact points and magnetic contact portions, each arranged in a first contact geometry for operative connection of the sensor unit (10) to the contact head (16), the sensor mat (12) has a multi-layered structure comprising:
(a) a lower layer (13) having a lower contact surface for contact on the body surface (20) and an upper contact surface for support of the sensor unit (10), whereby openings (15, 17) are provided which are aligned with respect to the at least one light detector device (2) of the sensor unit (10), and
(b) an upper layer (14), which is connected to the upper contact surface of the lower layer (13) such that the upper and lower layers (14, 13) are selectively detachable from one another; and the contact head (16) comprises:
(a) a ring-shaped second contact configured as an annular printed circuit board comprising contact pins as second electrical contacts and tin points as second magnetic contacts, each arranged in a second contact geometry that corresponds to the first contact geometry,
(b) a housing (40) for accommodating the ring-shaped second contact,
(c) an optical fiber (44) configured for guiding light from an external light source, and
(d) a cylindrical deflector (64) having a reflection surface (62) and a light-emitting surface (22).

2. The sensor configuration (1) according to claim 1, wherein the sensor unit (10) has one or more material thickenings (39) for stiffening the flexible printed circuit board.

3. The sensor configuration (1) according to claim 1, wherein the sensor unit (10) further comprises at least two tabs (38), wherein a first of the tabs (38) is oriented extending perpendicular to the longitudinal axis (18), and wherein a second of the tabs (38) is oriented extending along the longitudinal axis (18).

4. The sensor configuration (1) according to claim 1, wherein the contact head (16) further comprises electrical lines (42), which are fixable in the housing (40) and which are connectible to the second electrical contacts (46) in a conductive way.

5. The sensor configuration (1) according to claim 4, wherein:

the ring shaped second contact (47) comprises a first contact ring (48) with spring contact pins as the electrical contacts, and a second contact ring (49) with tin points as the magnetic contacts, the first contact ring (48) has a first side on which the spring pins (46) are provided in a predetermined configuration, and a second side on which connectors (52) are provided to form a plug contact (50) with a mating part provided on the electrical lines (42), and the second contact ring (49) has through-holes, through which the spring contact pins (46) extend, and a first side on which magnetic contacts (45) are disposed to contact the magnetic contact portions of the annular shaped first contact (30) of the sensor unit.

6. The sensor configuration (1) according to claim 1, wherein the optical fiber is either fixed in the housing (40) or in a retaining element accommodatable in the housing (40) and in contact with the deflector (64).

7. The sensor configuration (1) according to claim 1, wherein the reflection surface (62) is a closed beveled end face of the deflector.

8. The sensor configuration (1) according to claim 1, wherein the deflector (64) is, at least in part, a galvanized plastic element.

9. The sensor configuration (1) according to claim 1, wherein the deflector (64) is a hollow cylinder with a closed semispherical end face (66).

10. The sensor configuration (1) according to claim 9, wherein the deflector element (64) is made of a reflecting material.

11. The sensor configuration (1) according to claim 1, wherein the contact head (16) further comprises an energy source.

12. The sensor configuration (1) according to claim 1, further comprising an external control and processor.

13. Sensor configuration (1) for non-invasive measurement of parameters of a body tissue, the sensor configuration comprising:

a sensor unit (10), a sensor mat (12) for detachable placement of the sensor configuration (1) on a body surface (20) having the body tissue, and a contact head (16) detachably attached to the sensor unit (10), wherein:

the sensor unit (10) comprises:
(a) a flexible printed circuit board with conducting tracks (5) and a longitudinal axis (18),
(b) at least one light detector (2) for detecting light that has been emitted into the body tissue and has passed through the latter, and
(c) an annular shaped first contact (30) having electrical contact points and magnetic contact portions, each arranged in a first contact geometry for operative connection of the sensor unit (10) to the contact head (16), the sensor mat (12) has a multi-layered structure comprising:
(a) a lower layer (13), having a lower contact surface for contact on the body surface (20) and an upper contact surface for support of the sensor unit (10), whereby openings (15, 17) are provided which are aligned with respect to the at least one light detector (2) of the sensor unit (10), and
(b) an upper layer (14), which is connected to the upper contact surface of the lower layer (13) in a way detachable from one another, and the contact head (16) comprises:
(a) a ring-shaped second contact configured as an annular printed circuit board comprising contact pins as second electrical contacts and tin points as second magnetic contacts, each arranged in a second contact geometry that corresponds to the first contact geometry, (b) a housing (40) for accommodating the ring-shaped second contact, and (c) a cylindrical internal light source (70) made of a light-conducting material with a light-emitting surface (22) for guiding light from the internal light source.

14. The sensor configuration (1) according to claim 13, wherein the sensor unit (10) has one or more material thickenings (39) for stiffening the flexible circuit board.

15. The sensor configuration (1) according to claim 13, wherein the sensor unit (10) further comprises at least two tabs (38), wherein a first of the tabs (38) is oriented extending perpendicular to the longitudinal axis (18), and wherein a second of the tabs (38) is oriented extending along the longitudinal axis (18).

16. The sensor configuration (1) according to claim 1, wherein the contact head (16) further comprises elecrical lines (42), which are fixable in the housing (40) and which are connectible to the second electrical contacts (46) in a conductive way.

17. The sensor configuration (1) according to claim 13, wherein the contact head (16) further comprises an energy source.

\* \* \* \* \*

UNITED STATES PATENT AND TRADEMARK OFFICE
CERTIFICATE OF CORRECTION

| | |
|---|---|
| PATENT NO. | : 11,931,146 B2 |
| APPLICATION NO. | : 16/810387 |
| DATED | : March 19, 2024 |
| INVENTOR(S) | : Juerg Hans Froehlich et al. |

It is certified that error appears in the above-identified patent and that said Letters Patent is hereby corrected as shown below:

In the Claims

In Column 15, Line 17, Claim 16, delete "elecrical" and insert -- electrical --, therefor.

Signed and Sealed this
First Day of October, 2024

Katherine Kelly Vidal
*Director of the United States Patent and Trademark Office*